(12) United States Patent
Bailey

(10) Patent No.: US 7,651,061 B2
(45) Date of Patent: Jan. 26, 2010

(54) LIGHTED APPARATUS FOR SUPPORTING FLUID DISPENSERS

(76) Inventor: Ellen Bailey, 19866 Seagull Way, Saratoga, CA (US) 95070

( * ) Notice: Subject to any disclaimer, the term of this patent is extended or adjusted under 35 U.S.C. 154(b) by 363 days.

(21) Appl. No.: 11/341,187

(22) Filed: Jan. 28, 2006

(65) Prior Publication Data

US 2007/0176061 A1   Aug. 2, 2007

(51) Int. Cl.
*F16M 11/00* (2006.01)
(52) U.S. Cl. .................. 248/176.1; 211/85.13
(58) Field of Classification Search .............. 248/129, 248/146, 158, 176.1; 604/251, 259; 362/572, 362/573, 431; 211/85.13, 133, 207, 172, 211/119, 117
See application file for complete search history.

(56) References Cited

U.S. PATENT DOCUMENTS

| | | | | |
|---|---|---|---|---|
| 2,279,596 A * | 4/1942 | Schipper | ................. | 362/84 |
| 3,295,240 A * | 1/1967 | Garte | .................. | 40/473 |
| 4,038,982 A | 8/1977 | Burke et al. | ........... | 128/214 E |
| 4,685,912 A | 8/1987 | Jones | .................. | 604/247 |
| 4,822,344 A | 4/1989 | O'Boyle | ............. | 604/248 |
| 4,842,588 A | 6/1989 | Jones | .................. | 604/51 |
| 5,094,418 A * | 3/1992 | McBarnes et al. | ......... | 248/286.1 |
| 5,112,019 A * | 5/1992 | Metzler et al. | ........... | 248/405 |
| 5,379,200 A * | 1/1995 | Echard | .............. | 362/186 |
| 5,407,163 A | 4/1995 | Kramer et al. | ........... | 248/291 |
| 5,843,045 A * | 12/1998 | DuPont | ............. | 604/251 |
| 6,050,713 A * | 4/2000 | O'Donnell et al. | ......... | 362/551 |
| 6,079,678 A | 6/2000 | Schott et al. | ........... | 248/229.15 |
| 6,224,027 B1 * | 5/2001 | Johnson et al. | ......... | 248/125.8 |
| 6,359,381 B1 * | 3/2002 | Okuno et al. | ............ | 313/485 |
| 6,386,491 B1 * | 5/2002 | Bissett | ............... | 248/121 |
| 6,969,031 B2 | 11/2005 | Ugent et al. | ............ | 248/128.8 |
| 7,374,318 B2 * | 5/2008 | Brooks et al. | ........... | 362/396 |
| 2002/0096608 A1 * | 7/2002 | Cedarberg, III | ......... | 248/125.3 |
| 2004/0027826 A1 * | 2/2004 | Walden | ............... | 362/234 |
| 2005/0242701 A1 * | 11/2005 | Nomura et al. | ............ | 313/483 |

* cited by examiner

*Primary Examiner*—Alfred Joseph Wujciak, III
(74) *Attorney, Agent, or Firm*—Morgan, Lewis & Bockius LLP

(57) ABSTRACT

A substantially tubular supporting member oriented in a substantially vertical position, where a fluid dispenser holder is rotatably coupled to a top end of the supporting member and the fluid dispenser is movable rotationally clockwise or counterclockwise with respect to the supporting member into a plurality of rotational positions. In some embodiments, the supporting member may be mounted to a base connected proximate to a bottom end of the supporting member. The fluid dispenser holder has at least one hook attached to it, wherein the hook comprises a light source that may emit visible light.

12 Claims, 5 Drawing Sheets

LIGHTED APPARATUS FOR SUPPORTING FLUID DISPENSERS

TECHNICAL FIELD

The disclosed embodiments relate generally to fluid dispensers. More particularly, the disclosed embodiments relate to lighted apparatuses for fluid dispensers that are easy to see and use in various lighting conditions, and may include a rotary fluid dispenser holder that avoids tangles in the fluid delivery systems.

BACKGROUND

Medical patients often require intravenous ("IV") medication and hydration delivery systems. These IV systems generally utilize a vertical support pole located above the patient so that their contents may easily be administered with gravity flow. Depending on the patient's needs, multiple medications may be administered simultaneously through use of a plurality of fluid dispensers. In traditional IV systems, IV liquid delivery tubing can easily become tangled or wrapped around the support pole, particularly when multiple IV fluid dispensers are hung from the same support pole. Moreover, when multiple IV fluid dispensers are in use, the delivery tubing itself may become tangled together. These tangles can cause a host of problems, including patient discomfort caused by an IV line inadvertently being removed from the patient, requiring reinsertion. Where an IV line is not removed, the patient can experience discomfort when the medical attendant is untangling the tubing. Additionally, time spent untangling lines is an inefficient use of the medical attendant's time and skills.

Another issue with traditional IV systems is a lack of visibility in low light conditions, such as during the night, which can make changing IV bags difficult. Since patient care in hospital is necessarily carried out on a 24-hour-a-day basis, medical care attendants often change IV fluid dispensers during the night. Since patients may need to remain undisturbed by the attendant's actions, the option of simply turning on the room lighting to see the IV system may be unavailable or inappropriate. Where it is possible to turn on the light, such an action risks waking a sleeping patient, which could have a detrimental impact on the patient. Moreover, the tangling issue in a low light setting is exacerbated, increasing the risk and impact of the problems disclosed above.

Traditional IV systems therefore have at least the disadvantages of being: 1) difficult to manage when a plurality of fluid dispensers is in use at once; 2) difficult to maintain in low lighting situations; and 3) prone to causing patient discomfort when multiple lines become tangled.

The present invention overcomes these limitations and disadvantages, and the impact of these problems with an IV pole featuring a rotating top portion combined with a light source emitted from the pole itself.

SUMMARY

The present invention relates to an IV pole that overcomes the limitations and disadvantages described above by providing a substantially tubular supporting member oriented in a substantially vertical position, where a fluid dispenser holder is rotatably coupled to a top end of the supporting member and the fluid dispenser is movable rotationally clockwise or counterclockwise with respect to the supporting member into a plurality of rotational positions. In some embodiments, the supporting member may be mounted to a base connected proximate to a bottom end of the supporting member. The fluid dispenser holder has at least one hook attached to it, wherein the hook comprises a light source that may emit visible light.

One embodiment is an apparatus for supporting fluid dispensers which has a substantially tubular pole, which is the supporting member for the fluid dispensers. The pole is preferentially hollow and oriented in a substantially vertical position, although the pole can be angled, comprised of rods oriented to form an inner recess, telescoping sections or, less preferentially, a solid pole structure. Preferentially, atop the supporting member is a holder for fluid dispensers. The holder is rotatably coupled to the supporting member. In one embodiment, the holder can be fixed in place or a variable resistance can be applied such that the holder will only rotate when a force is applied that is greater than the resistance force. The holder preferentially includes one or a plurality of arms to hold a fluid dispenser. The arms preferentially have at least one hook-shaped or pronged portion oriented such that a fluid dispenser can be hung from the holder arm. Proximate the bottom portion of the supporting member is a base portion, which may optionally be rotatably connected. If rotatably coupled or connected, it is preferable that such connection is lockable such that the bottom portion will not rotate, as rotation from the base could cause tangling problems, not solve such problems. A light source is also located on the apparatus for multiple benefits, such as for reading dispenser bag labels, reading charts and notes, and for use in aiding the untangling of tubes. Alternatively or additionally, the light may emit from the support member. The holder is connected to allow for both clockwise or counterclockwise into a number of rotational positions throughout a full circular range.

Such lighted apparatuses for supporting fluid dispensers provide more easily manageable fluid dispensing systems that are easy to use in low light and which avoid patient discomfort.

BRIEF DESCRIPTION OF THE DRAWINGS

For a better understanding of the aforementioned aspects of the invention as well as additional aspects and embodiments thereof, reference should be made to the Detailed Description of Embodiments below, in conjunction with the following drawings in which like reference numerals refer to corresponding parts throughout the figures.

DETAILED DESCRIPTION OF EMBODIMENTS

Apparatuses for rotatable lighted fluid dispensers are described. Reference will be made to certain embodiments of the invention, examples of which are illustrated in the accompanying drawings. While the invention will be described in conjunction with the embodiments, it will be understood that it is not intended to limit the invention to these particular embodiments alone. On the contrary, the invention is intended to cover alternatives, modifications and equivalents that are within the spirit and scope of the invention as defined by the appended claims.

Moreover, in the following description, specific details are set forth to provide a thorough understanding of the present invention. However, it will be apparent to one of ordinary skill in the art that the invention may be practiced without these particular details. In other instances, methods, procedures, and components that are well-known to those of ordinary skill in the art are not described in detail to avoid obscuring aspects of the present embodiments of the inventions.

Figure 1:
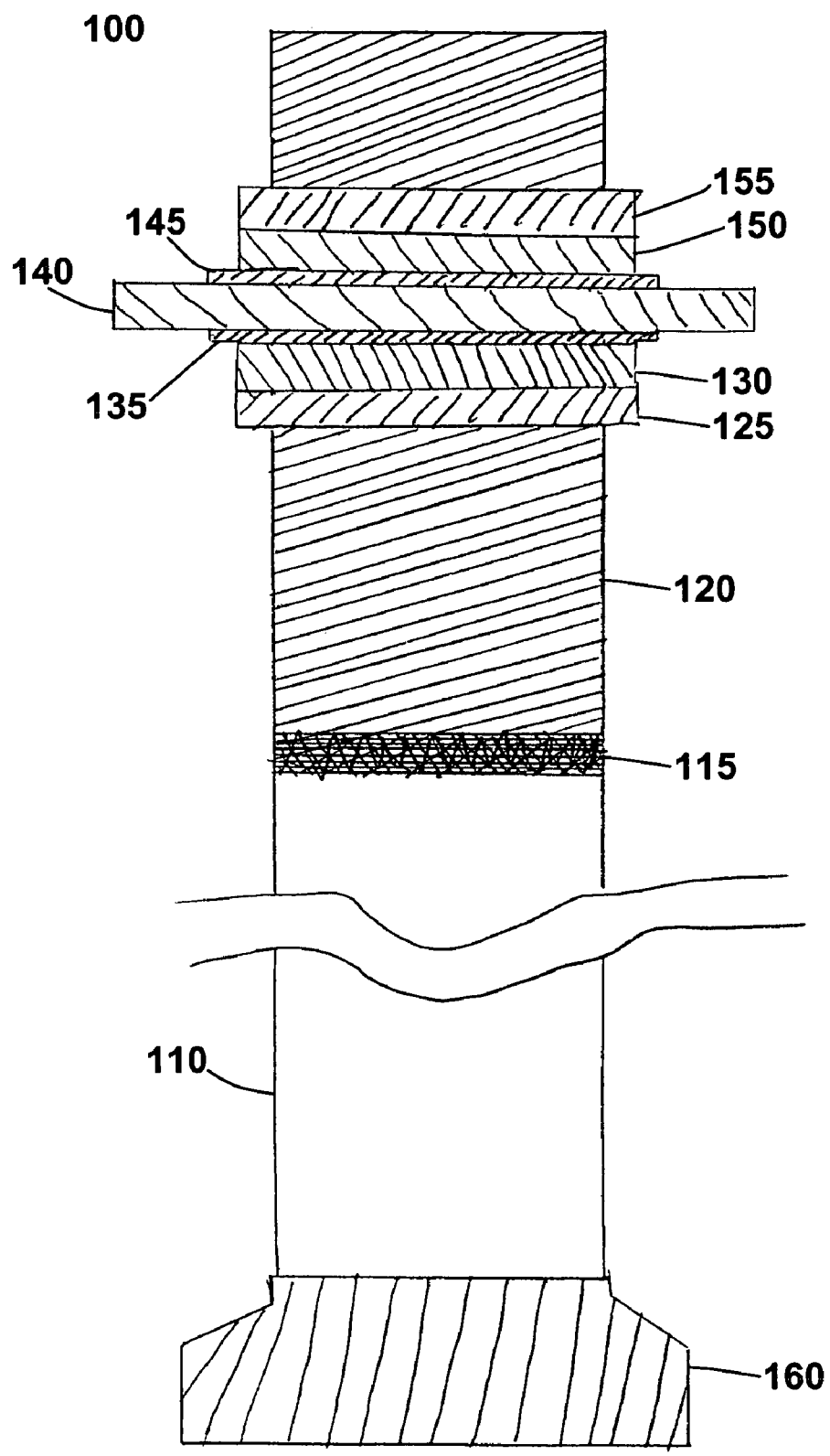
FIG. 1 is a diagram illustrating an exemplary tubular supporting member in accordance with one embodiment of the present invention.
Figure 4A:
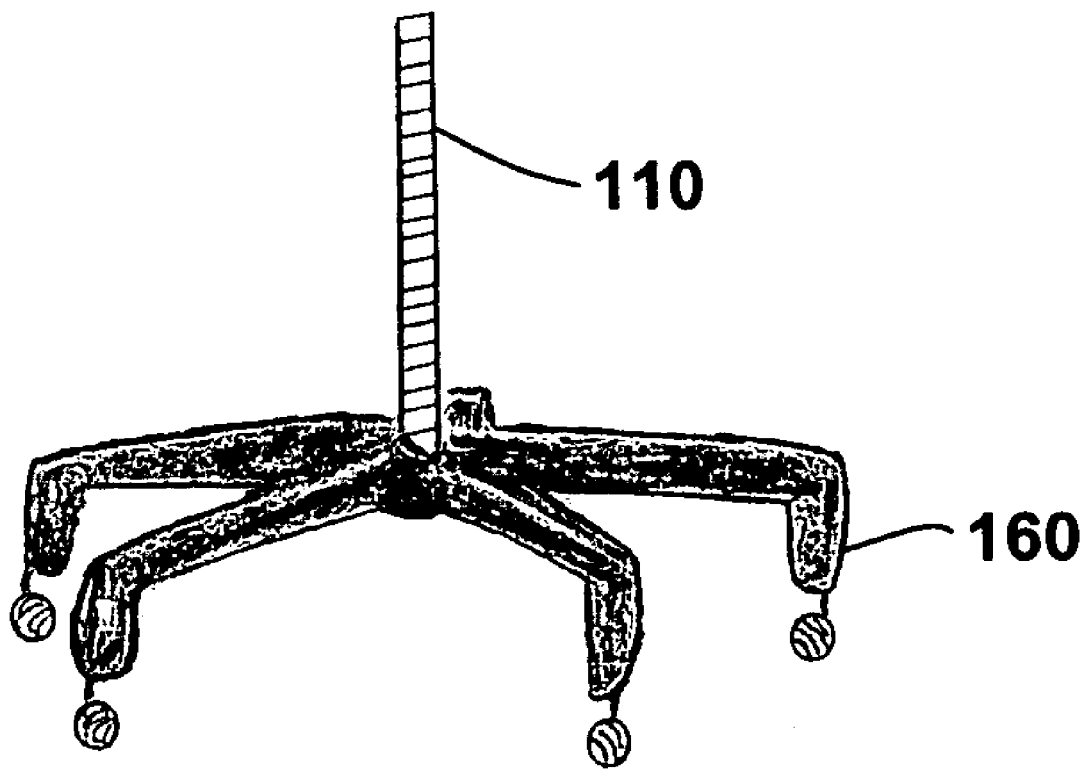
FIG. 4 is a diagram illustrating an exemplary fluid dispenser system incorporating the supporting member of FIG. 1.

FIG. 1 is a diagram illustrating an exemplary fluid dispenser supporting structure 100; for purposes of clarity, the actual hooks or other means for holding fluid dispensers are not depicted in this figure. According to one embodiment of the invention, a base 160 may be connected to the bottom of substantially tubular supporting member 110, which is thereby supported in a substantially vertical position. In other embodiments of the invention, base 160 may have a conventional plurality of three or more legs extending away from supporting member 110. In yet other embodiments, base 160 may further have conventional integral casters or other similar devices as shown in FIG. 4a that permit the structure 100 to be easily moved to different locations where a patient may require medication or hydration. In some embodiments, supporting structure 100 has no base 160 mounted to support member 110. This allows mounting of fluid dispenser supporting structure 100 on many devices, such as a gurney, hospital bed, operating room table, or a wheel chair.

Figure 4B:
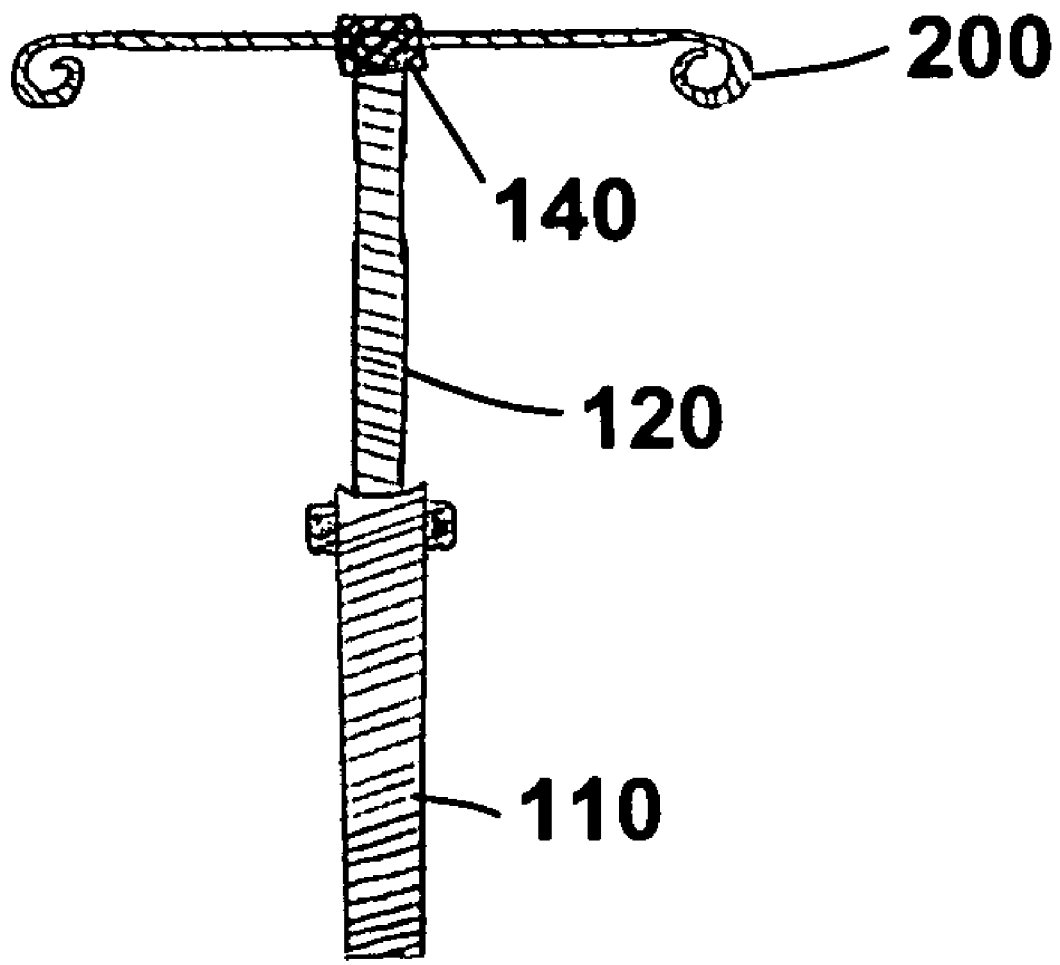

FIG. 1 depicts an exemplary embodiment of the present invention that permits rotation of the fluid dispenser holder 140 with respect to the supporting member 110. Supporting member 110 is joined 115 by any appropriate means to a threaded rod 120 such as those available from Threadall Manufacturing Company. The junction 115 between supporting member 110 and threaded rod 120 may be any appropriate method such as welding, casting, threaded insertion, etc. In other possible embodiments, such as in FIG. 4b, threaded rod 120 may be smaller in diameter than support member 110. In other embodiments, the entire length of the supporting member upon which fluid dispenser 140 is mounted may be threaded. On threaded rod 120, two lock nuts 125 and 130 are mounted, above which a washer 135 may be set. Over washer 135, fluid dispenser holder 140 is set in place, and a washer 145 and two lock nuts 150 and 155 are screwed in place onto threaded rod 120. After tightening lock nut pair 125 and 130 and lock nut pair 150 and 155 in light of the talent possessed by one of ordinary skill in the art, a simple friction clutch mechanism is established so that fluid dispensing member 140 may easily be rotated clockwise or counterclockwise with respect to supporting member 110 into a plurality of positions. This rotational capability facilitates easy, tangle-free maintenance of multiple fluid dispensers by medical attendants, and thus avoids patient discomfort.

In other embodiments the rotational capability of fluid dispensing member 140 may be established through any of a number of devices, including without limitation, bearings, motors, servos, or other friction clutch designs. In some embodiments, the fluid dispenser holder and fluid dispensers may rotate in a horizontal plane without substantial vertical displacement.

Figure 2:
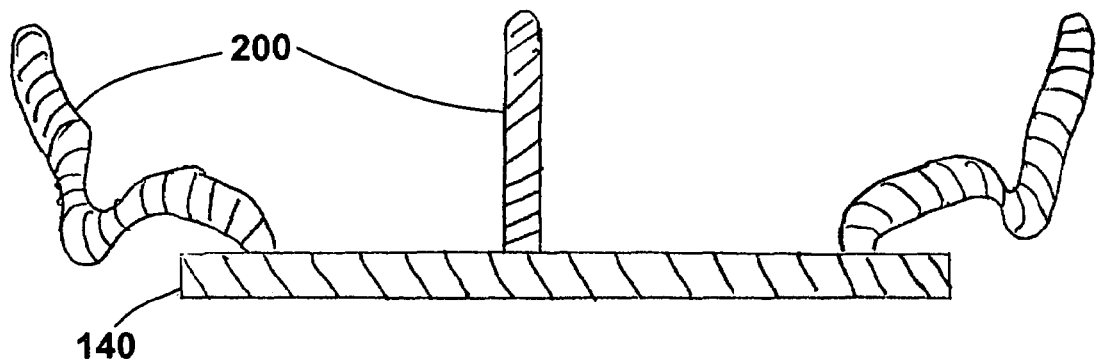
FIG. 2 is a diagram illustrating an exemplary fluid dispenser holder embodiment of the present invention.

FIG. 2 depicts fluid dispensing holder 140, upon which is attached one or a plurality of mounts such as hooks 200. The hook(s) 200 are intended to hold fluid dispensers, such as IV bags. In some embodiments, there may be one hook 200 mounted on fluid dispensing holder 140. In other embodiments, there may be two or more hooks 200 mounted on fluid dispensing holder 140. Any suitable method of joining fluid dispensing holder 140 with hook(s) 200 may be used given appropriate skill in the art. In yet other embodiments, fluid dispensing holder 140 and hook(s) 200 may be formed from one piece of material.

The foregoing components may be made of any material suitable for generally sterile medical care environments such as metal, plastics, fiberglass, composites, etc.

Figure 3:
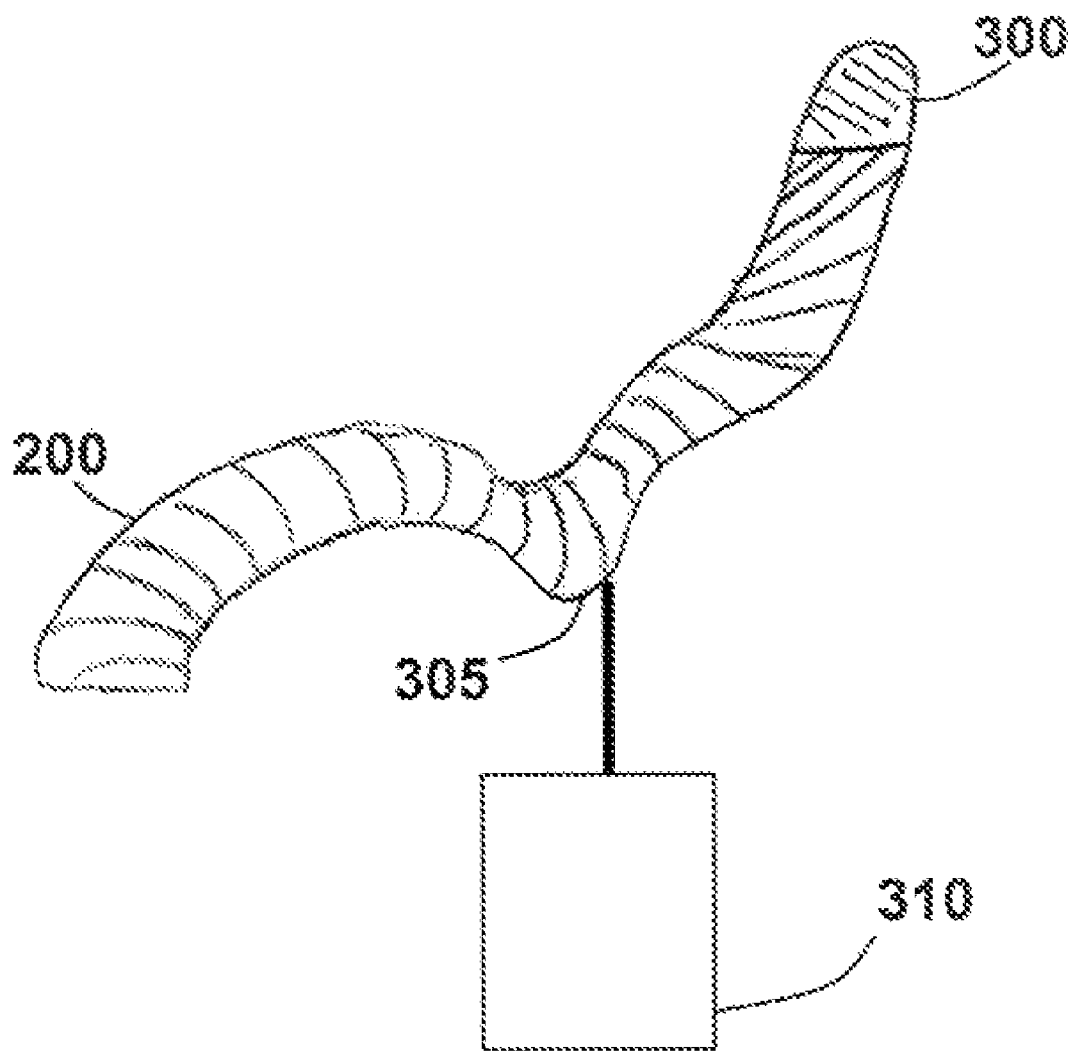
FIG. 3 is a diagram illustrating an exemplary fluid dispenser holder.

FIG. 3 depicts one exemplary hook 200. In various embodiments, different shapes of hooks may be utilized such as the conventional shape shown in FIG. 4b. For instance, FIG. 3 depicts a hook 200 with a curve 305 configured for receiving a fluid dispenser 310, e.g. a hanging IV bag, so that the position of the dispenser will be stabilized and horizontally displaced from fluid dispensing holder 140. This horizontal displacement may facilitate rotating fluid dispensing holder 140 around supporting member 110. In other embodiments, hook 200 may be a smoothly inwardly descending sloping curve so that a fluid dispenser will rest upon the outer circumference of fluid dispensing holder 140.

In an exemplary embodiment, at least a portion of hook 200 includes a light source 300, which emits light in visible wavelengths. Light source 300 emits light so that an attendant may easily find the hook 200 to permit adding or changing a fluid dispenser in low light conditions. In some embodiments, the light emitting source 300 may be a cap configured to engage the tip of the hook. In other embodiments, the light emitting source 300 is integral with or internal to the hook 200. Accordingly, hook 200 may be made of any material suitable for generally sterile medical care environments such as metal, plastics (opaque, translucent, or transparent), or others so long as sufficient structural strength is provided for supporting the weight of a full fluid dispenser. An appropriate material for hook 200 may selected in part based on the type of light source 300 used.

Light source 300 may be arranged on hook 200 to extend for the entire length of the hook or for only a portion or portions of the hook, such as the tip and/or curve 305. Accordingly, each hook may have a single or multiple locations containing a light source 300. In one preferred embodiment, light source 300 is provided on the tip of hook 200.

Many sources may provide light source 300's emitted light. For example, light source 300 may be phosphorescence which glows-in-the-dark, light-emitting diodes, light bulbs (incandescent, fluorescent, halogen, etc.), or any other appropriate means. Light source 300 may be powered by any of a multitude of possible sources, such as DC electric batteries (e.g., single use or rechargeables with or without an AC/DC transformer), AC electric power, or any suitable photoluminescent material such as, without limitation, strontium aluminate, magnesium strontium silicate, or zinc sulfide, or any other form of phosphor-based irradiation, nuclear powered reactions, or light generating reaction. In some embodiments, a potentiometer or a rheostat or any other current regulation device may be utilized to regulate light source 300's brightness. Accordingly, it is contemplated that a conventional dimmer circuit may be provided with an adjustment knob or switch to allow a user to regulate the brightness of the light source. The lights may be individually controlled to light one light source at a time, to minimize patient disturbance. Further, a light shield or shade feature can be used to block light from emitting toward the patient while maintaining the ability to easily read the fluid dispenser and perform work relating to such dispenser. Optionally, a retractable light element can be used to extend the light from the fluid dispenser holder or other location of the light. Such an extension can be particularly useful in controlling the light emission to provide light where needed, while preventing unnecessary light disturbance where light is unwanted.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. An apparatus for supporting fluid dispensers comprising:
    a substantially tubular supporting member oriented in a substantially vertical position;
    a fluid dispenser holder rotatably coupled to a top end of the supporting member and movable rotationally with respect to the supporting member;
    a base connected proximate to a bottom end of the supporting member;
    at least one hook attached to the fluid dispenser holder, the hook comprising a light source that emits visible light, wherein the light source is integral with the hook; and
    at least one fluid dispenser held by the holder, wherein the fluid dispenser may be moved clockwise or counterclockwise into a plurality of rotational positions, and the fluid dispenser is removable from the holder.

2. The apparatus of claim 1, wherein the light source is disposed on a tip of the hook.

3. The apparatus of claim 2, wherein the light source is a cap configured to engage the tip of the hook.

4. The apparatus of claim 1, wherein the fluid dispenser is an IV bag.

5. The apparatus of claim 1, wherein the visible light is from an electric light source.

6. The apparatus of claim 1, wherein the visible light is from a phosphorescent source.

7. The apparatus of claim 1, wherein the visible light is from strontium aluminate.

8. The apparatus of claim 1, wherein the fluid dispenser holder may rotate in a horizontal plane without substantial vertical displacement.

9. The apparatus of claim 1, further comprising a plurality of legs connected with a bottom end of the supporting member.

10. The apparatus of claim 1, wherein the light source is internal to the hook.

11. The apparatus of claim 1, wherein the light source extends for the entire length of the hook.

12. The apparatus of claim 1, wherein the light source extends for a portion of the length of the hook.

* * * * *